(12) United States Patent
Manchekar (10) Patent No.: US 10,723,676 B2
(45) Date of Patent: Jul. 28, 2020

(54) METHODS AND SYSTEMS FOR PRODUCING 1,3-BUTADIENE

(71) Applicant: SABIC Global Technologies B.V., Bergen op Zoom (NL)

(72) Inventor: Arun Vasant Manchekar, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/061,898

(22) PCT Filed: Dec. 13, 2016

(86) PCT No.: PCT/IB2016/057566
§ 371 (c)(1),
(2) Date: Jun. 13, 2018

(87) PCT Pub. No.: WO2017/103776
PCT Pub. Date: Jun. 22, 2017

(65) Prior Publication Data
US 2018/0370875 A1    Dec. 27, 2018

Related U.S. Application Data

(60) Provisional application No. 62/269,873, filed on Dec. 18, 2015.

(51) Int. Cl.
*B01D 3/14* (2006.01)
*C07C 7/08* (2006.01)
(Continued)

(52) U.S. Cl.
CPC ............... *C07C 7/08* (2013.01); *B01D 3/141* (2013.01); *B01D 3/148* (2013.01); *B01D 3/40* (2013.01);
(Continued)

(58) Field of Classification Search
CPC .......... B01D 3/141; B01D 3/148; B01D 3/40; B01D 3/42; B01D 5/006; C07C 7/08; C07C 11/167
See application file for complete search history.

(56) References Cited

U.S. PATENT DOCUMENTS 2,993,841 A    7/1961  Sarno ........................ 202/39.5
4,134,795 A    1/1979  Howat ........................ 203/53
(Continued)

FOREIGN PATENT DOCUMENTS

| JP | H1057704 | 2/2006 |
| RU | 2330005 C2 | 7/2008 |
| WO | WO2009120181 A1 | 10/2009 |

OTHER PUBLICATIONS

International Search Report and Written Opinion from PCT/IB2016/057566, dated Feb. 17, 2017, 9 pages.
(Continued)

*Primary Examiner* — Jonathan Miller
(74) *Attorney, Agent, or Firm* — Norton Rose Fulbright US LLP (57) ABSTRACT

The present disclosure provides methods and systems for producing 1,3-butadiene. In certain embodiments, the present disclosure provides methods for the extractive distillation of 1,3-butadiene in a divided wall distillation column having a first region, a second region and a combined bottom region. An exemplary method can include feeding a $C_4$ hydrocarbon stream and a first solvent into the first region and removing a first stream from the first region. The method can further include feeding a second solvent into the second region, removing a second stream that includes 1,3-butadiene from the second region, and removing a third stream from the combined bottom region.

16 Claims, 4 Drawing Sheets (51) Int. Cl.
*B01D 3/40* (2006.01)
*B01D 3/42* (2006.01)
*B01D 5/00* (2006.01)
*C07C 11/167* (2006.01)

(52) U.S. Cl.
CPC .............. *B01D 3/42* (2013.01); *B01D 5/006* (2013.01); *C07C 11/167* (2013.01)

(56) References Cited

U.S. PATENT DOCUMENTS

| | | | | |
|---|---|---|---|---|
| 6,250,106 | B1* | 6/2001 | Agrawal | B01D 3/14 62/643 |
| 7,132,038 | B2* | 11/2006 | Bohner | B01D 3/14 203/1 |
| 7,226,527 | B2* | 6/2007 | Bohner | B01D 3/141 203/2 |
| 7,417,173 | B2 | 8/2008 | Crone et al. | 585/325 |
| 7,462,277 | B2* | 12/2008 | Adrian | B01D 3/141 208/115 |
| 7,482,500 | B2* | 1/2009 | Johann | C07C 5/333 585/325 |
| 7,528,290 | B2 | 5/2009 | Zimmermann et al. | 585/809 |
| 7,556,717 | B2* | 7/2009 | Heida | B01D 3/141 203/27 |
| 7,557,257 | B2* | 7/2009 | Heida | C07C 7/08 203/2 |
| 7,619,126 | B2* | 11/2009 | Heida | C07C 7/08 203/1 |
| 7,692,053 | B2* | 4/2010 | Heida | C07C 7/08 203/1 |
| 8,222,474 | B2 | 7/2012 | Bridges et al. | 585/810 |
| 2005/0199482 | A1 | 9/2005 | Heida | 203/50 |
| 2006/0021911 | A1 | 2/2006 | Adrian et al. | 208/115 |
| 2009/0105514 | A1* | 4/2009 | Lee | B01D 3/40 585/808 |
| 2009/0139852 | A1* | 6/2009 | Vannuland | B01D 3/14 203/49 |
| 2018/0154278 | A1* | 6/2018 | Lee | B01D 3/00 |

OTHER PUBLICATIONS

Kiss et al. "Energy efficient control of a BTX dividing-wall column." Computers and Chemical Engineering 35 (2011) 2896-29043.

Kolbe et al. "Novel distillation concepts using one-shell columns." Chem. Eng. and Process., 43 (2004) 339-346.

Lei et al. "Process improvement on separating C4 by extractive distillation." Chemical Engineering Journal 85 (2002) 379-386.

Wagner et al. "BASF Process for Production of Pure Butadiene." Ind. Eng. Chem., 62(4):43-48 (1970).

White, Wm. Claude. "Butadiene production process overview." Chemico-Biological Interactions 166 (2007) 10-14.

Yang et al. "Simulation of 1,3-Butadiene Production Process by Dimethylfomamide Extractive Distillation." Separation Science and Engineering, *Chinese Journal of Chemical Engineering*, 17(1) 27-35 (2009).

* cited by examiner

```
┌─────────────────────────────────────┐
│ Providing a divided wall distillation column that │ ─── 401
│ includes a longitudinal wall dividing the column  │
│ into a first region, a second region and a        │
│ combined bottom region                            │
└─────────────────────────────────────┘
              ↓
┌─────────────────────────────────────┐
│ Providing a hydrocarbon stream to the first       │ ─── 402
│ region of the distillation column                 │
└─────────────────────────────────────┘
              ↓
┌─────────────────────────────────────┐
│ Feeding a first solvent into the first            │ ─── 403
│ region of the distillation column                 │
└─────────────────────────────────────┘
              ↓
┌─────────────────────────────────────┐
│ Removing a first stream from the first region of  │ ─── 404
│ the distillation column                           │
└─────────────────────────────────────┘
              ↓
┌─────────────────────────────────────┐
│ Transferring a first reflux fluid to the first region │ ─── 405
│ of the distillation column                        │
└─────────────────────────────────────┘
              ↓
┌─────────────────────────────────────┐
│ Feeding a second solvent into the second          │ ─── 406
│ region of the distillation column                 │
└─────────────────────────────────────┘
              ↓
┌─────────────────────────────────────┐
│ Removing a second stream from the second          │ ─── 407
│ region of the distillation column                 │
└─────────────────────────────────────┘
              ↓
┌─────────────────────────────────────┐
│ Transferring a second reflux fluid to the second  │ ─── 408
│ region of the distillation column                 │
└─────────────────────────────────────┘
              ↓
┌─────────────────────────────────────┐
│ Removing a third stream from the combined         │ ─── 409
│ bottom region of the distillation column          │
└─────────────────────────────────────┘
              ↓
┌─────────────────────────────────────┐
│ Separating 1,3-butadiene from the third stream    │ ─── 410
│ and recycling 1,3-butadiene back to the           │
│ combined bottom region of the distillation        │
│ column                                            │
└─────────────────────────────────────┘
              ↓
┌─────────────────────────────────────┐
│ Adding a polymerization inhibitor to one or more  │ ─── 411
│ of the first region, second region, and combined  │
│ bottom region of the distillation column          │
└─────────────────────────────────────┘
```

METHODS AND SYSTEMS FOR PRODUCING 1,3-BUTADIENE

CROSS-REFERENCE TO RELATED APPLICATIONS

This application is a national phase application under 35 U.S.C. § 371 of International Application No. PCT/IB2016/057566 filed Dec. 13, 2016, which claims priority to U.S. Provisional Patent Application No. 62/269,873 filed Dec. 18, 2015. The entire contents of each of the above-referenced disclosures is specifically incorporated by reference herein without disclaimer.

FIELD

The present disclosure relates to methods and systems for producing 1,3-butadiene.

BACKGROUND 1,3-butadiene is a major product of the petrochemical industry. Its simple chemical structure combined with its low molecular weight and high chemical reactivity makes it a very useful building block in the synthesis of other materials. 1,3-butadiene can be used as a monomer starting material for preparation of various polymers, including synthetic rubbers. 1,3-butadiene can also be used as a feedstock in the production of adiponitrile or as a substrate in certain Diels-Alder reactions.

1,3-butadiene can be obtained from different sources, including dehydrogenation of n-butane and the reaction of ethanol. 1,3-butadiene can also be isolated from $C_4$ hydrocarbon streams, e.g., $C_4$ fractions obtained from the steam cracking of naphtha, gas (e.g., ethane, propane, butane and liquid petroleum gas (LPG)) cracking, the catalytic cracking of gas oil and/or vacuum gas oil, the catalytic dehydrogenation of butane and butene, and the oxidative dehydrogenation of butene. $C_4$ hydrocarbons streams can include $C_4$ alkanes, e.g., butane, isobutane; $C_4$ alkenes, e.g., isobutene, 1-butene, trans-2-butene, cis-2-butene; $C_4$ alkadienes, e.g., 1,3-butadiene, 1,2-butadiene, and/or $C_4$ alkynes, e.g., vinylacetylene, ethylacetylene, dimethylacetylene. In some embodiments, the $C_4$ hydrocarbon streams can also include a $C_3$ alkyne such as methylacetylene. Due to the low differences in the relative volatilities of such compounds, the isolation of crude 1,3-butadiene from a $C_4$ fraction can be complicated and is generally carried out by extractive distillation.

Certain methods and systems for purifying 1,3-butadiene are known in the art. U.S. Pat. No. 7,556,717 discloses methods for extractive distillation using a divided wall distillation column, where a stream containing 1,3-butadiene and solvent can be obtained from the common bottom region of the column. Japanese Patent No. JPH1057704 describes the use of a divided wall distillation column for the separation of a multicomponent feedstream. U.S. Pat. No. 7,462,277 discloses methods and systems for extractive distillation of a $C_4$ hydrocarbon stream that includes the use of a divided wall distillation column to remove butanes from the top of the first region, butenes are removed from the top of the second region and 1,3-butadiene is removed from the combined bottom region of the column. U.S. Pat. No. 7,528,290 discloses the use of a divided wall distillation column for the separation of 1-butene from a mixed $C_4$ hydrocarbon stream. U.S. Pat. No. 7,619,126 discloses methods and systems for the distillation of 1,3-butadiene from a $C_4$ hydrocarbon stream, which includes the use of a divided wall distillation column that is coupled to an extractive scrubbing column. U.S. Pat. No. 7,692,053 disclose methods and systems for the distillation of 1,3-butadiene from a $C_4$ hydrocarbon stream, that include the use of a divided wall column that is coupled to an extractive wash column and/or an acetylenes outgasser column.

There remains a need in the art for methods and systems for producing 1,3-butadiene.

SUMMARY

The presently disclosed subject matter provides methods and systems for extractive distillation of 1,3-butadiene.

The presently disclosed subject matter provides methods for producing 1,3-butadiene from a $C_4$ hydrocarbon stream. In certain embodiments, a method can include providing a distillation column that comprises a longitudinal wall dividing the distillation column into a first region, a second region and a combined bottom region, and which further includes a first condenser, a second condenser and a reboiler. The method can include feeding a $C_4$ hydrocarbon stream including one or more of $C_4$ alkanes, $C_4$ alkenes, $C_4$ alkadienes, $C_4$ alkynes, and combinations thereof into the first region of the distillation column. The $C_4$ hydrocarbon stream can split into two or more streams and the two or more streams can be fed into two or more locations in the first region. Methods can further include feeding a first solvent into the first region of the distillation column, removing a first stream from the first region of the distillation column, feeding a second solvent into the second region of the distillation column, removing a second stream from the second region of the distillation column, and removing a third stream from the combined bottom region of the distillation column.

In certain embodiments, a method for extractive distillation of 1,-3 butadiene can include providing a distillation column that includes a longitudinal wall dividing the distillation column into a first region, a second region and a combined bottom region, and further includes a first and second condenser and a reboiler. The method can include feeding a $C_4$ hydrocarbon stream that includes one or more of 1,3-butadiene, butane, isobutane, 1-butene, trans-2-butene, cis-2-butene, isobutene, 1,2-butadiene, vinylacetylene, ethylacetylene and methylacetylene into the first region of the distillation column and feeding a first solvent into the first region of the distillation column. The method can further include removing a first stream that includes isobutene, butane, isobutane, 1-butene, trans-2-butene and cis-2-butene from an upper section of the first region of the distillation column. In certain embodiments, the method includes feeding a second solvent into the second region of the distillation column and removing a second stream that includes 1,3-butadiene and/or 1,2-butadiene from an upper section of the second region of the distillation column. In certain embodiments, the method can further include removing a third stream containing vinylacetylene, ethylacetylene, methylacetylene, the first solvent and/or the second solvent from the combined bottom region of the distillation column.

In certain embodiments, the $C_4$ hydrocarbon stream can be fed into a middle section of the first region of the distillation column. The $C_4$ hydrocarbon stream can be split into two or more streams prior to feeding it into the first region of the distillation column. The two or more streams can be fed to two or more locations in the first region. In certain embodiments, the first solvent can be fed into an upper section of the first region of the distillation column. In certain embodiments, the first stream can be removed from the first region of the distillation column using a first condenser. In certain embodiments, the second stream can be removed from the second region of the distillation column using a second condenser. In certain embodiments, the second stream includes 1,2-butadiene. The second stream can include greater than about 93% w/w 1,3-butadiene. In certain embodiments, the first and/or second solvent includes acetonitrile.

In certain embodiments, the methods can further include transferring a first reflux fluid from the first condenser to the first region of the distillation column. In certain embodiments, the methods can further include transferring a second reflux fluid from the second condenser to the second region of the distillation column.

In certain embodiments, the third stream can further include 1,3-butadiene. The method can include separating 1,3-butadiene, the first solvent and/or the second solvent from the third stream and recycling 1,3-butadiene, the first solvent and/or the second solvent back to the combined bottom region of the distillation column. In certain embodiments, 1,3-butadiene, the first solvent and/or the second solvent can be separated from the third stream by vaporization.

In certain embodiments, the first region of the distillation column can have at least about 75 equilibrium stages. In certain embodiments, the second region of the distillation column can have at least about 70 equilibrium stages. In certain embodiments, the upper section of the first region and/or second region of the distillation column has a pressure of about −1.0 to about 15.0 bar. In certain embodiments, the combined bottom region of the distillation column has a pressure of about −1.0 to about 15 bar. The pressure drop between the combined bottom region and an a top section of the first region and/or second region can be from about 0.01 to about 2.0 bar.

In certain embodiments, a method for extractive distillation of 1,3-butadiene from a $C_4$ hydrocarbon stream can include providing a distillation column that includes a longitudinal wall dividing the distillation column into a first region, a second region and a combined bottom region, a first and second condenser and a reboiler. The method can further include feeding a $C_4$ hydrocarbon stream containing isobutene, 1,3-butadiene, 1,2-butadiene, butane, isobutane, 1-butene, trans-2-butene, cis-2-butene, vinylacetylene, ethylacetylene, and methylacetylene into the first region of the distillation column. In certain embodiments, the method can further include feeding acetonitrile into the first region of the distillation column and removing a first stream that includes isobutene, butane, isobutane, 1-butene, trans-2-butene and cis-2-butene from an upper section of the first region of the distillation column. In certain embodiments, the method can further include feeding acetonitrile into the second region of the distillation column and removing a second stream containing at least about 90% w/w of 1,3-butadiene from an upper section of the second region of the distillation column. In certain embodiments, the method includes removing a third stream containing vinylacetylene, ethylacetylene, methylacetylene and acetonitrile from the combined bottom region of the distillation column.

In certain embodiments, a method for extractive distillation of 1,3-butadiene from a hydrocarbon stream can include providing a distillation column that includes a longitudinal wall dividing the distillation column into a first region, a second region and a combined bottom region, a first and second condenser and a reboiler. The method can include feeding a $C_4$ hydrocarbon stream that includes 1,3-butadiene, 1,2-butadiene, isobutane, butane, isobutane, 1-butene, trans-2-butene, cis-2-butene, vinylacetylene, ethylacetylene, and methylacetylene into a middle section of the first region of the distillation column. In certain embodiments, the method can further include feeding acetonitrile into an upper section of the first region of the distillation column and removing a first stream containing butane, isobutane, isobutene, 1-butene, trans-2-butene and cis-2-butene from an upper section of the first region of the distillation column via a first condenser. The method can include transferring a first reflux fluid from the first condenser to the first region of the distillation column. In certain embodiments, the method can include feeding acetonitrile into an upper section of the second region of the distillation column. The method can further include removing a second stream that includes at least about 90% w/w of 1,3-butadiene from an upper section of the second region of the distillation column via a second condenser and transferring a second reflux fluid from the second condenser to the second region of the distillation column. In certain embodiments, the method can include removing a third stream containing vinylacetylene, ethylacetylene, methylacetylene, 1,3-butadiene and acetonitrile from the combined bottom region of the distillation column and separating vinylacetylene from the acetonitrile, separating 1,3-butadiene and/or acetonitrile from the third stream and recycling 1,3-butadiene and/or acetonitrile back to the combined bottom region of the distillation column.

DETAILED DESCRIPTION

The presently disclosed subject matter provides methods and systems for producing 1,3-butadiene.

Figure 1:
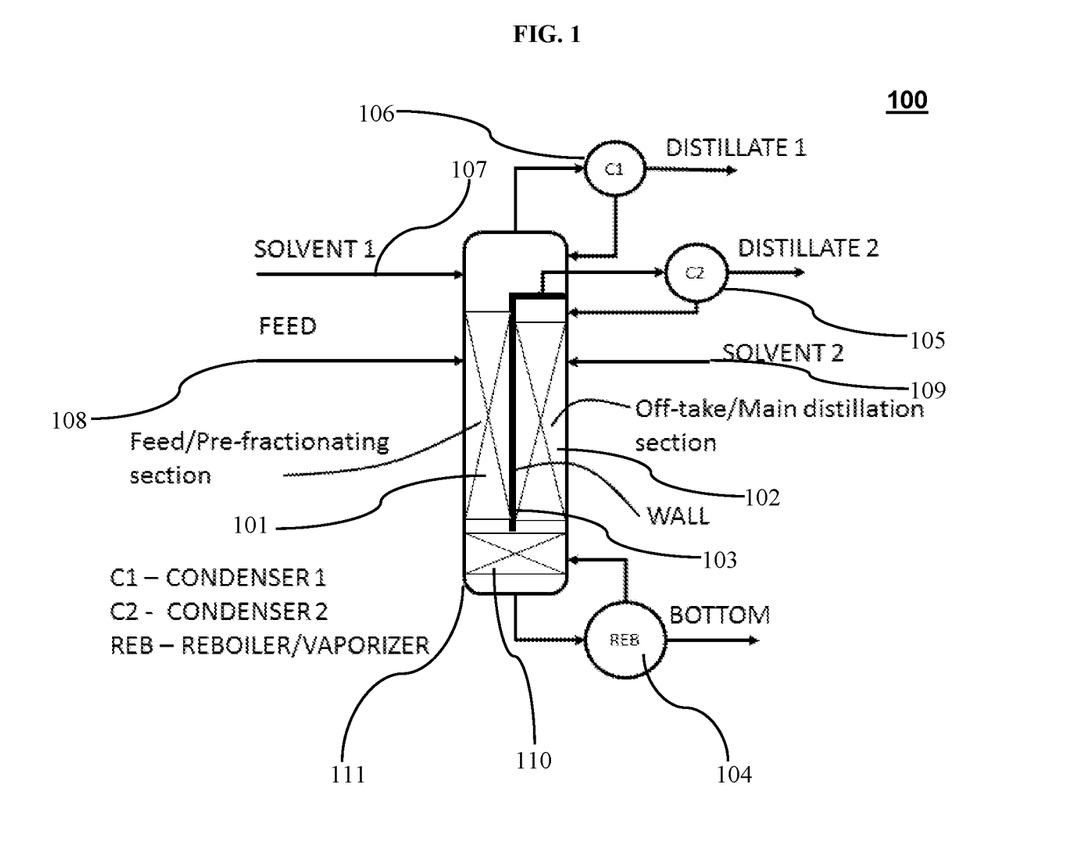
FIG. 1 depicts a system for producing 1,3-butadiene according to one exemplary embodiment of the disclosed subject matter.

The presently disclosed subject matter provides a system for the production of 1,3-butadiene from hydrocarbon feed streams, e.g., $C_4$ hydrocarbon streams. For the purpose of illustration and not limitation, FIG. 1 is a schematic representation of an exemplary system according to a non-limiting embodiment of the disclosed subject matter. In certain embodiments, the system 100 can include a divided wall distillation column 111.

The divided wall distillation column 111 can include a longitudinal wall 103 dividing the column into at least three regions. For example, the longitudinal wall can be fixed or movable. The longitudinal wall can be welded to the interior of the distillation column and/or attached with fittings and/or fasteners. The longitudinal wall can include gaskets and/or sealing to form a gas- and/or liquid-tight barrier.

In certain embodiments, the divided wall distillation column 111 can include a first region 101. In certain embodiments, the first region can have a constant width along the height of the divided wall distillation column. In other certain embodiments, the width of the first region can vary, i.e., the longitudinal wall 103 can be slanted. The first region 101 of the divided wall distillation column 111 can include from about 50 to about 100 equilibrium stages, e.g., about 75 stages. In certain embodiments, the first region can be staged, e.g., with bubble cap, valve, chimney, and/or sieve trays. The first region can be randomly packed with a packing material, e.g., raschig rings, pall rings, berl saddles and/or intalox saddles. or can include structured packing, e.g., with metal sheets or gauze. In certain embodiments, an upper section of the first region of the divided wall distillation column 101 can be coupled to a first condenser 106. By way of example, the first condenser can be a heat exchanger, e.g., a shell and tube heat exchanger, pipe in pipe heat exchanger, spiral heat exchanger, or plate heat exchanger. For example, and not by way of limitation, the first region can be coupled to the first condenser via one or more transfer lines, e.g., for returning a reflux fluid from the condenser back to the first region 101 of the divided wall distillation column 111.

"About" or "approximately" as used herein mean within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

"Coupled" as used herein refers to the connection of a system component to another system component by any means known in the art. The type of coupling used to connect two or more system components can depend on the scale and operability of the system. For example, and not by way of limitation, coupling of two or more components of a system can include one or more joints, valves, transfer lines or sealing elements. Non-limiting examples of joints include threaded joints, soldered joints, welded joints, compression joints and mechanical joints. Non-limiting examples of fittings include coupling fittings, reducing coupling fittings, union fittings, tee fittings, cross fittings and flange fittings. Non-limiting examples of valves include gate valves, globe valves, ball valves, butterfly valves and check valves.

In certain embodiments, the divided wall distillation column 111 can include a second region 102. The second region can have a constant or varied width along the height of the divided wall distillation column, depending on the orientation of the longitudinal wall 103. The second region 102 of the divided wall distillation column 111 can include from about 50 to about 100 equilibrium stages, e.g., about 70 stages. The second region can be staged e.g., with bubble cap, valve, chimney, and/or sieve trays, and/or packed, e.g., with a packing material and/or metal sheets or gauze. In certain embodiments, the second region 102 of the divided wall distillation column 111 can be coupled to a second condenser 105, e.g., for separating a second stream from the distillation column 111. By way of example, the second condenser can be a heat exchanger, For example, and not by way of limitation, an upper section of the second region 102 can be coupled to the second condenser 105 via one or more transfer lines, e.g., for returning a reflux fluid from the condenser back to the second region 102 of the divided wall distillation column 111.

In certain embodiments, the divided wall distillation column 111 can include a combined bottom region 110, e.g., for separating vinylacetylene, ethylacetylene, methylacetylene and/or solvents from the hydrocarbon streams. The combined bottom region 110 can be in fluid communication with the first region 101 and/or the second region 102 of the divided wall distillation column 111. In certain embodiments, the combined bottom region 110 can be coupled to a reboiler 104, e.g., for heating the hydrocarbon streams during distillation. By way of example, the reboiler can be a thermosiphon, kettle, or fired heater. In certain embodiments, the combined bottom region 110 can be coupled to a reboiler 104 via one or more transfer lines, e.g., for returning a solvent, or other components present within the hydrocarbon stream (such as 1,3-butadiene), from the reboiler to the combined bottom region 110 of the divided wall distillation column 111.

The system 100 can further include one or more feed lines, e.g., 208, coupled to the first region 101 of the divided wall distillation column 111. The one or more feed lines 208 can be used to feed a hydrocarbon stream, e.g., a C4 hydrocarbon stream, into the distillation column. In certain embodiments, the feed line 208 can be coupled to a middle section of the first region 101 of the divided wall distillation column 111.

In certain embodiments, the system 100 can further include one or more solvent feed lines, e.g., 207 and/or 209, for feeding a solvent into the distillation column. For example, and not by way of limitation, the system 100 can include a first solvent feed line 207 coupled to the first region 101, e.g., an upper section of the first region, of the divided wall distillation column 111. In certain embodiments, the first solvent feed line 207 can be used to feed a first solvent into the first region 101 of the divided wall distillation column 111. In certain embodiments, the system 100 can include a second solvent feed line 209 coupled to the second region 102, e.g., an upper section of the second region, of the divided wall distillation column 111 for feeding a second solvent into the divided wall distillation column 111.

The system of the present disclosure can further include additional components and accessories including, but not limited to, one or more gas exhaust lines, cyclones, product discharge lines, reaction zones, heating elements, control valves, control systems, decanters, reflux pumps, splitters, safety valves, vacuum pumps, vacuum ejectors, heat exchangers, startup/shutdown arrangements, manholes, sample points, pumparounds, and one or more measurement and/or control accessories. The one or more measurement accessories can be any suitable measurement accessory known to one of ordinary skill in the art including, but not limited to, pH meters, flow monitors, pressure indicators, pressure transmitters, differential pressure transmitters, thermowells, temperature-indicating controllers, gas detectors, analyzers, viscometers, level transmitters, level switches, level gauges, component analyzers, sight glass, light glass and density meters. The components and accessories can be placed at various locations within the system.

In accordance with the embodiments of the presently disclosed subject matter, the system and the various components and accessories that can be included in the system, e.g., the divided wall distillation column, can be made out of a plurality of suitable materials. Suitable materials include, but are not limited to, aluminum, stainless steel, carbon steel, glass-lined materials, ceramics, polymer-based materials including fluorinated polymer-lined materials, nickel-base metal alloys, cobalt-based metal alloys, Hastelloy™ or combinations thereof.

Figure 2:
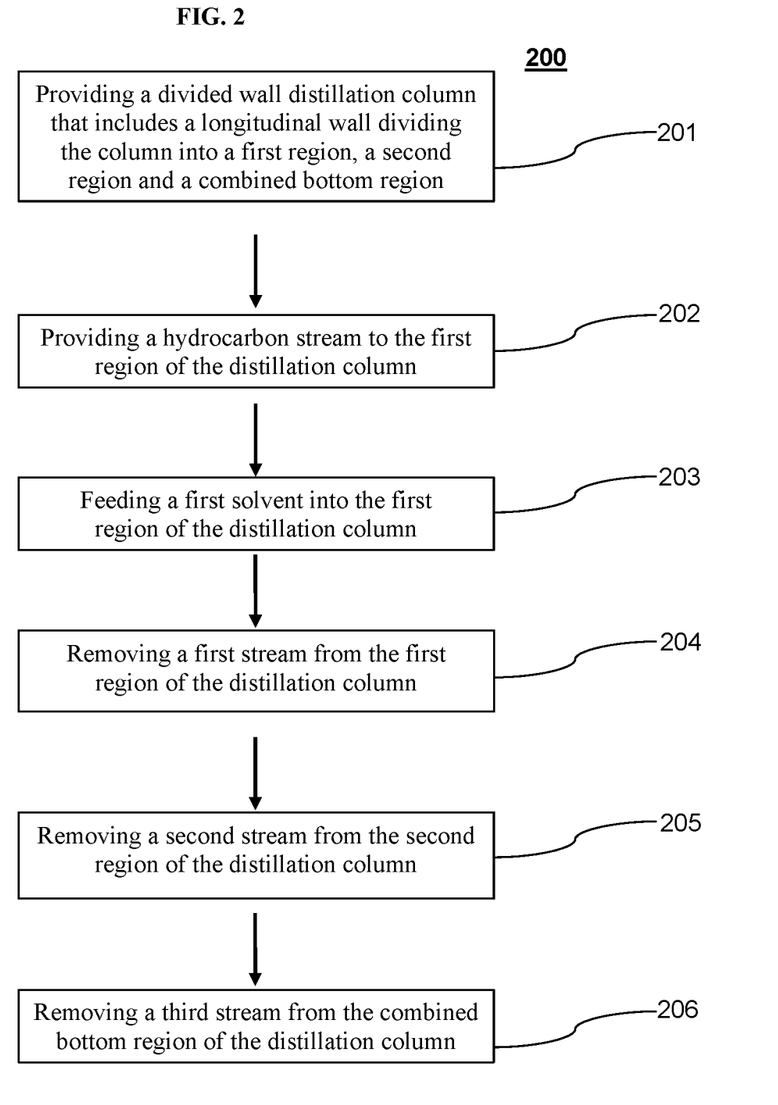
FIG. 2 depicts a method for producing 1,3-butadiene according to one exemplary embodiment of the disclosed subject matter.

The presently disclosed subject matter further provides methods for producing 1,3-butadiene. For example, and not by way of limitation, the presently disclosed subject matter provides methods for distilling 1,3-butadiene from a hydrocarbon stream, e.g., by solvent-mediated distillation. For the purpose of illustration and not limitation, FIG. 2 is a schematic representation of an exemplary method according to the disclosed subject matter. In certain embodiments, the method 200 can include providing a divided wall distillation column that includes a longitudinal wall dividing the column into a first region, a second region and a combined bottom region 201. In certain embodiments, the distillation column is coupled to one or more reboilers and/or two or more condensers as disclosed above (see, e.g., FIG. 1).

In certain embodiments, the method 200 can include providing a hydrocarbon stream 202, e.g., to one or more regions of the distillation column. For example, and not by way of limitation, the hydrocarbon stream can be fed into a middle section of the first region of the distillation column. Alternatively or additionally, the hydrocarbon stream can be fed into an upper section of the first region of the distillation column. In certain embodiments, the hydrocarbon stream can be split and various portions can be fed to one or more sections of the first region of the distillation column.

In certain embodiments, the hydrocarbon stream is a $C_4$ hydrocarbon stream. For example, and not by way of limitation, a $C_4$ hydrocarbon stream can be generated by steam cracking of naphtha, gas (e.g., ethane, propane, butane and liquid petroleum gas (LPG)) cracking, fluid catalytic cracking (FCC) of gas oil and/or vacuum gas oil, catalytic dehydrogenation of butane and butene, and oxidative dehydrogenation of butene. The hydrocarbon stream can include olefins, paraffins and/or 1,3-butadiene. For example, and not by way of limitation, the hydrocarbon stream can include 1,3-butadiene, 1,2-butadiene, isobutene, normal butane (n-butane), isobutane, 1-butene, trans-2-butene, cis-2-butene, vinylacetylene, ethylacetylene, methylacetylene or combinations thereof. In certain embodiments, the hydrocarbon stream further can include propylene and/or propane.

In certain embodiments, the hydrocarbon stream can include from about 5% to about 60% w/w of 1,3-butadiene, about 0.001% to about 1.0% w/w of 1,2-butadiene, from about 2% to about 10% w/w of n-butane, from about 0.001% to about 10% w/w of isobutane, from about 20% to about 40% w/w of 1-butene, from about 2% to about 15% w/w of 2-butene (e.g., trans-2-butene and/or cis-2-butene), from about 0.1% to about 10% w/w of isobutene, from about 0.01% to about 1% w/w of vinylacetylene, from about 0.01% to about 1% w/w of ethylacetylene and/or from about 0.01% to about 1% w/w of methylacetylene. A non-limiting example of a hydrocarbon stream for use in the presently disclosed subject matter is provided in Table 2.

In certain embodiments, the method 200 can further include feeding a first solvent into the distillation column 203. In certain embodiments, the first solvent can be fed into the first region of the distillation column. The first solvent can be fed into an upper section of the first region of the distillation column. In certain embodiments, the first solvent can be fed to the distillation column at a flow rate that is proportional to the flow rate of the hydrocarbon stream. For example, the ratio of the flow rate of the first solvent to the flow rate of the hydrocarbon stream can be from about 1 w/w to about 15 w/w, from about 3 w/w to about 12 w/w, or about 8 w/w. In certain embodiments, the first solvent can be a solvent in which butanes and butenes, e.g., within the $C_4$ hydrocarbon stream, are less soluble as compared to 1,3-butadiene and/or a solvent in which $C_4$ alkynes, such as vinylacetylene, ethylacetylene and methylacetylene, are more soluble as compared to 1,3-butadiene. Non-limiting examples of the first solvent include acetonitrile, dimethylformamide, furfural, N-methyl-2-pyrrolidone, acetone, dimethylacetamide, diethylformamide, butyrolactone or combinations thereof. See, for example, Wagner and Weitz, Ind. Eng. Chem., 62(4):43-48 (1970), U.S. Pat. Nos. 2,993,841, 4,134,795, 4,277,313, 7,417,173 and 8,222,474.

In certain embodiments, the method 200 can include removing a first stream from the first region of the distillation column 204. The first stream can be removed through the use of a first condenser at an upper section of the first region of the distillation column. In certain embodiments, the first stream includes the lower molecular weight and/or the hydrocarbons present within the hydrocarbon feed that are less soluble in the first solvent. For example, and not by way of limitation, the first stream can include butane, isobutane, isobutene, 1-butene, trans-2-butene and/or cis-2-butene. In certain embodiments, the first stream can include from about 5% to about 15% w/w n-butane, from about 0.1% to about 15% w/w isobutane, from about 0.1% to about 5% w/w isobutene, from about 20% to about 80% w/w 1-butene and/or from about 10% to about 25% w/w 2-butene (e.g., cis-2-butene and/or trans-2-butene). In certain embodiments, the first stream can further include from about 1% to about 5% w/w of 1,3-butadiene.

In certain embodiments, extraction of the first stream from the hydrocarbon stream in the presence of the first solvent can be performed at a temperatures ranging from about 20° C. to about 200° C. For example, the temperature at the top of the first region can be from about 20° C. to about 80° C., from about 40° C. to about 60° C., or about 54° C. The temperature at the bottom of the first region can be from about 50° C. to about 200° C., from about 75° C. to about 125° C., or about 109° C. In certain embodiments, extraction can be performed at pressures from about −1 bar (i.e., in a vacuum) to about 15 bar. In particular embodiments, the pressure can be from about 6 bar to about 8 bar.

In certain embodiments, the method can include transferring a first reflux fluid from the first condenser to the first region of the distillation column. The flow rate of the first reflux fluid can depend, e.g., on the composition of the hydrocarbon stream, the desired purity of 1,3-butadiene, and operating conditions. In certain embodiments, the first reflux fluid can contain 1,3-butadiene, which can be recycled to the first region of the distillation column from the first condenser. The first reflux fluid can further include butane, isobutane, isobutene, 1-butene, trans-2-butene and/or cis-2-butene. In certain embodiments, the descending stream of the first solvent can include additional components of the hydrocarbon stream, e.g., 1,3-butadiene, 1,2-butadiene, vinylacetylene, ethylacetylene, and/or methylacetylene, which are more soluble in the solvent than the components within the first stream.

This descending stream of the first solvent can be transferred to the reboiler via the combined bottom region of the divided wall distillation column. In certain embodiments, the stream that enters the reboiler can be vaporized within the reboiler and the vapor fraction that contains 1,3-butadiene and/or 1,2-butadiene, can be recycled back to the combined bottom region for distillation within the second region of the divided wall distillation column. In certain embodiments, vinylacetylene, ethylacetylene, methylacetylene and/or the first solvent can be removed from the divided wall distillation column as a third stream as described below. The combined bottom region can have a pressure from about −1 bar (i.e., in a vacuum) to about 15 bar. In certain embodiments, the pressure drop between the combined bottom region and the top of the first region can be from about 0.01 bar to about 2 bar.

The method 200 can further include removing a second stream from the second region of the distillation column in the presence of a second solvent 105. Non-limiting examples of the second solvent include acetonitrile, dimethylformamide, furfural, N-methyl-2-pyrrolidone, acetone, dimethylacetamide, diethylformamide, butyrolactone or combinations thereof. In certain embodiments, the second solvent can be mixed with a co-solvent. For example, the co-solvent can be water. See, for example, U.S. Pat. No. 7,556,717. In certain embodiments, the first solvent and the second solvent can be the same solvent. For example, and not by way of limitation, the first solvent and second solvent can be acetonitrile. Alternatively, the first and second solvent can be different. In certain embodiments, the second solvent can be fed into the second region of the distillation column, e.g., within the upper section and/or middle section of the second region of the column. In certain embodiments, the second solvent can be fed to the distillation column at a flow rate that is proportional to the flow rate of the hydrocarbon stream. For example, the ratio of the flow rate of the second solvent to the flow rate of the hydrocarbon stream can be from about 1 w/w to about 15 w/w, from about 3 w/w to about 12 w/w, or about 9 w/w.

In certain embodiments, the second stream can be removed through the use of the second condenser at the top of the second region of the distillation column. In certain embodiments, the second stream includes 1,3-butadiene. For example, and not by way of limitation, the second stream can include greater than about 90% w/w 1,3-butadiene. In certain embodiments, the second stream can include greater than about 91% w/w 1,3-butadiene, greater than about 92% w/w 1,3-butadiene, greater than about 93% w/w 1,3-butadiene, greater than about 94% w/w 1,3-butadiene, greater than about 95% w/w 1,3-butadiene, greater than about 96% w/w 1,3-butadiene, greater than about 97% w/w 1,3-butadiene, greater than about 98% w/w 1,3-butadiene or greater than about 99% w/w 1,3-butadiene. In certain embodiments, the method can include adding a 1,3-butadiene polymerization inhibitor to one or more of the first, second and combined bottom regions to increase the purity of 1,3-butadiene. For example, a suitable 1,3-butadiene polymerization inhibitor can include p-tert-butylcatechol (TBC). See, for example, Yang et al., Chinese J. Chem. Eng., 17(1) 27-35 (2009). The purified 1,3-butadiene obtained from the methods and systems of the present disclosure can be used for applications demanding high purity 1,3-butadiene. In certain embodiments, the second stream can further include 1,2-butadiene, e.g., from about 0.1% to about 10%. In certain embodiments, the second stream can further include isobutene, e.g., from about 0.1 parts per billion (ppb) to about 20 ppb, 1-butene, e.g., from about 1 ppb to about 50 ppb, 2-butene, e.g., from about 5 ppb to about 5,000 ppb, vinylacetylene, e.g., less than about 0.1 ppb, ethylacetylene, e.g., less than about 0.1 ppb, and/or methylacetylene, e.g., less than about 0.1 ppb.

In certain embodiments, extraction of the second stream in the presence of the second solvent can be performed at a temperatures ranging from about 20° C. to about 200° C. For example, the temperature at the top of the second region can be from about 20° C. to about 80° C., from about 40° C. to about 60° C., or about 54° C. The temperature at the bottom of the second region can be from about 50° C. to about 200° C., from about 125° C. to about 175° C., or about 152° C. In certain embodiments, extraction can be performed at a pressure from about −1 bar (i.e., in a vacuum) to about 15 bar. In particular embodiments, the pressure can be from about 6 bar to about 8 bar. In certain embodiments, the descending stream of the second solvent can include additional components of the hydrocarbon stream, e.g., vinylacetylene, ethylacetylene, methylacetylene, which are more soluble in the solvent than the components within the second stream, e.g., 1,3-butadiene. The descending stream of the second solvent can be transferred to the reboiler via the combined bottom region of the divided wall distillation column. The pressure drop between the combined bottom region and the top of the second region can be from about 0.01 bar to about 2 bar. As described above, the stream that enters the reboiler can be vaporized and a vapor fraction containing 1,3-butadiene and/or 1,2-butadiene can be recycled back to the combined bottom region. Vinylacetylene, ethylacetylene, methylacetylene and/or the second solvent can be removed from the divided wall distillation column as a third stream as described below.

In certain embodiments, the method can include transferring a second reflux fluid from the second condenser to the second region of the divided wall distillation column. In certain embodiments, the second reflux fluid can include vinylacetylene, ethylacetylene and methylacetylene, which can be transferred back to the second region of the divided wall distillation column via the second condenser. In certain embodiments, the second reflux fluid can further include other components, such as 1,3-butadiene, 1,2-butadiene, isobutene, 1-butene, trans-2-butene and/or cis-2-butene.

In certain embodiments, the method 200 can further include removing a third stream from the distillation column 206. The third stream can be removed from the combined bottom region of the distillation column as described above. In certain embodiments, the third stream can include vinylacetylene, ethylacetylene, methylacetylene, the first solvent and/or the second solvent, e.g., acetonitrile, or a combination thereof. For example, and not by way of limitation, the third stream can include from about 1 ppm to about 5,000 ppm of vinylacetylene, from about 1 ppm to about 5,000 ppm of ethylacetylene, and/or from about 1 ppm to about 5,000 ppm of methylacetylene. In certain embodiments, the method can further include separating vinylacetylene from the first solvent and/or second solvent and transferring the separated first solvent and/or second solvent to the combined bottom region of the distillation column.

Figure 4:
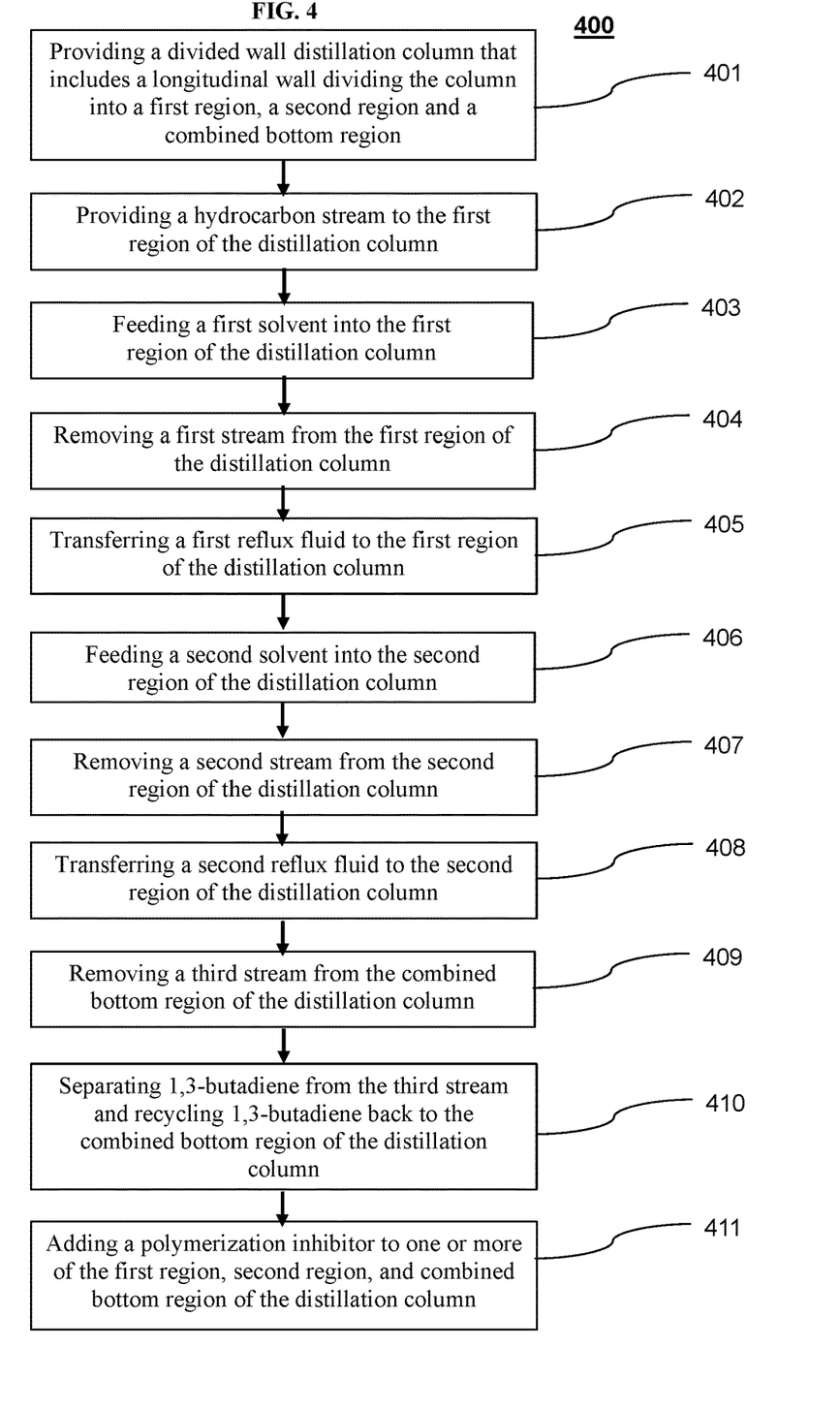
FIG. 4 depicts a method for producing 1,3-butadiene according to one exemplary embodiment of the disclosed subject matter.

For purposes of illustration, and not limitation, FIG. 4 is a schematic representation of an exemplary method for producing 1,3-butadiene according to the disclosed subject matter. The method 400 can include providing a divided wall distillation column that includes a longitudinal wall dividing the column into a first region, a second region and a combined bottom region 401. The distillation column can further include a first condenser coupled to the first region, a second condenser coupled to the second region and a reboiler coupled to the combined bottom region. The method can further include providing a hydrocarbon stream to the first region of the distillation column 402 and feeding a first solvent into the first region of the distillation column 403. For example, the hydrocarbon stream can include isobutene, 1,2-butadiene, 1,3-butadiene, butane, isobutane, 1-butene, trans-2-butene, cis-2-butene, vinylacetylene, ethylacetylene, and/or methylacetylene. The first solvent can include acetonitrile.

In certain embodiments, the method 400 can further include removing a first stream from the first region of the distillation column 404. The first stream can be removed via a first condenser. The first stream can include isobutene, butane, isobutane, 1-butene, trans-2-butene and/or cis-2-butene. The method can further include transferring a first reflux fluid to the first region of the distillation column 405, e.g., from the first condenser. The first reflux fluid can include isobutene, butane, isobutane, 1-butene, trans-2-butene and/or cis-2-butene.

In certain embodiments, the method 400 can further include feeding a second solvent into the second region of the distillation column 406. For example, the second solvent can be acetonitrile. The method can further include removing a second stream from the second region of the distillation column 407. The second stream can be removed by a second condenser. The second stream can include greater than about 90% 1,3-butadiene. The method can further include transferring a second reflux fluid to the second region of the distillation column 408, e.g., from the second condenser.

In certain embodiments, the method 400 can further include removing a third stream from the combined bottom region of the distillation column 409. For example, the third stream can include vinylacetylene, ethylacetylene, methylacetylene, 1-3 butadiene, the first solvent and/or the second solvent. The method can further include separating 1,3-butadiene from the third stream and recycling 1,3-butadiene back to the combined bottom region of the distillation column 410. Separating 1,3-butadiene from the third stream can include vaporizing a portion of the third stream. In certain embodiments, the first solvent and/or the second solvent can also be separated from the third stream and recycled with the 1,3-butadiene.

In certain embodiments, the method 400 can further include adding a polymerization inhibitor to one or more of the first region, second region, and combined bottom region of the distillation column 411.

The methods and systems of the presently disclosed subject matter can have numerous advantages over certain existing technologies, including improved reliability, reduced capital costs and consistency of the purified 1,3-butadiene product. The methods and systems of the present disclosure can also consume less energy, which can improve efficiency and reduce costs.

The following examples are merely illustrative of the presently disclosed subject matter and should not be considered as limiting in any way.

Example 1: Use of a Divided Wall Distillation Column to Produce 1,3-Butadiene This Example describes the manufacture of 1,3-butadiene from a $C_4$ hydrocarbon stream using a divided wall distillation column. FIG. 1 depicts the divided wall distillation column that was used in this Example, which includes a first region (referred to herein as the pre-fractionating section), a second region (referred to herein as the main distillation section) and a combined bottom region. The column further includes two condensers and a single reboiler. Details regarding the divided wall distillation column model are provided in Table 1.

A $C_4$ hydrocarbon stream was fed to the pre-fractionating section of the divided wall distillation column as the FEED and acetonitrile was fed to the pre-fractionating section as stream SOLVENT1. The contents of the $C_4$ hydrocarbon stream are shown in Table 2. A stream containing predominantly butane, butene-1, trans-2-butene and cis-2-butene was removed from the top of the first region of the column as a stream DISTILLATE1 (Table 2). Acetonitrile was then fed to the main distillation section as stream SOLVENT2. A stream containing predominantly acetonitrile and vinylacetylene was removed from the bottom of the combined bottom region of the column as stream BOTTOM (Table 2). The hydrocarbon stream containing 1,3-butadiene was removed from the top of the main distillation section as stream DISTILLATE2 (Table 2). The material balance and distillation column profiles of the disclosed divided wall distillation column method are provided in Table 2 and the column profiles of the disclosed divided wall distillation column method are shown in Table 6. The Wilson-Redlich Kwong thermodynamic model was used to estimate all properties. As shown in Table 2, the disclosed method resulted in a product stream (DISTILLATE2) that included 93% 1,3-butadiene.

TABLE 1

Model details of Divided Wall Distillation Column Process

| Equipment name | Pre-fractionating column | Main distillation column |
|---|---|---|
| Model Type | Radfrac | Radfrac |
| No. equilibrium stages | 75 | 70 |
| C4 Feed stage location | 40 | — |
| Condenser | Total | Total |
| Reboiler | Kettle | Kettle |
| Top Pressure | 7 bar | 7 bar |
| Bottom Pressure | 7.5 bar | 7.5 bar |
| Feed flowrate | 1000 kg/hr | — |
| Solvent flowrate | 8000 kg/hr | 9000 kg/hr |
| Solvent feed stage location | 3 | 3 |
| Reflux ratio | 11 | 5.55 |
| Boilup ratio | — | 0.36 |

TABLE 2

Material Balance of Divided Wall Distillation Column Method

| | FEED | SOLVENT 1 | DISTILLATE 1 | SOLVENT 2 | DISTILLATE 2 | BOTTOM |
|---|---|---|---|---|---|---|
| Temperature (° C.) | 50 | 50 | 54.1 | 50 | 55.8 | 152 |
| Pressure bar | 1 | 2 | 7 | 2 | 7 | 7.5 |
| Vapor Fraction | 1 | 0 | 0 | 0 | 0 | 0 |
| Mole Flow (kmol/hr) | 18.1 | 150.763 | 10.829 | 169.608 | 7.244 | 320.396 |
| Mass Flow (kg/hr) | 1000 | 8000 | 606.105 | 9000 | 391.435 | 17002.37 |
| Volume Flow (cm³/hr) | 477.679 | 10.015 | 1.069 | 11.267 | 0.67 | 25.864 |
| Enthalpy (MMBtu/hr) | 0.812 | 21.157 | −0.134 | 23.801 | 0.658 | 48.84 |
| MASS FLOW (kg/hr) | | | | | | |
| Acetonitrile | | 8000 | 43.702 | 9000 | 21.894 | 16934.34 |
| Water | | | | | | |
| N-butane | 58 | | 58 | | trace | trace |
| Iso-butene | 11.7 | | 11.7 | | trace | trace |

TABLE 2-continued

Material Balance of Divided Wall Distillation Column Method

|  | FEED | SOLVENT 1 | DISTILLATE 1 | SOLVENT 2 | DISTILLATE 2 | BOTTOM |
|---|---|---|---|---|---|---|
| Butene-1 | 374.7 |  | 374.7 |  | <0.001 | trace |
| Trans-2-butene | 51.6 |  | 51.6 |  | <0.001 | trace |
| Cis-2-butene | 40 |  | 39.982 |  | 0.017 | <0.001 |
| 1,3-butadiene | 453 |  | 26.408 |  | 365.755 | 60.819 |
| 1,2-butadiene | 4 |  | 0.013 |  | 3.769 | 0.218 |
| Vinylacetylene | 7 |  | trace |  | trace | 7 |
|  |  |  | MASS FRACTION |  |  |  |
| Acetonitrile |  | 1 | 0.072 | 1 | 0.056 | 0.996 |
| Water |  |  |  |  |  |  |
| N-butane | 0.058 |  | 0.096 |  | trace | trace |
| Iso-butene | 0.012 |  | 0.019 |  | 6 ppb | trace |
| Butene-1 | 0.375 |  | 0.618 |  | 29 ppb | trace |
| Trans-2-butene | 0.052 |  | 0.085 |  | 668 ppb | trace |
| Cis-2-butene | 0.04 |  | 0.066 |  | 44 ppm | 28 ppb |
| 1,3-butadiene | 0.453 |  | 0.044 |  | 0.934 | 0.004 |
| 1,2-butadiene | 0.004 |  | 21 ppm |  | 0.01 | 13 ppm |
| Vinylacetylene | 0.007 |  | trace |  | trace | 412 ppm |

Example 2: Comparative Example

This Example compares the method for producing 1,3-butadiene from a $C_4$ hydrocarbon stream using a divided wall distillation column disclosed herein to a method for producing 1,3-butadiene using two distinct distillation columns in series. Model details regarding the two distillation column system is shown in Table 3.

TABLE 3

Model Details of the Two Distillation Column System

| Equipment name | B1 | B2 |
|---|---|---|
| Model Type | Radfrac | Radfrac |
| No. equilibrium stages | 75 | 60 |
| C4 Feed stage location | 40 | 50 |
| Condenser | Total | Total |
| Reboiler | Kettle | Kettle |
| Top Pressure | 7 bar | 6 bar |
| Bottom Pressure | 7.5 bar | 6.4 bar |
| Feed flowrate | 1000 kg/hr | — |
| Solvent flowrate | 8000 kg/hr | 8000 kg/hr |
| Solvent feed stage location | 2 | 3 |
| Reflux ratio | 28 | 1.5 |
| Boilup ratio | 1.3 | 0.3 |

Figure 3:
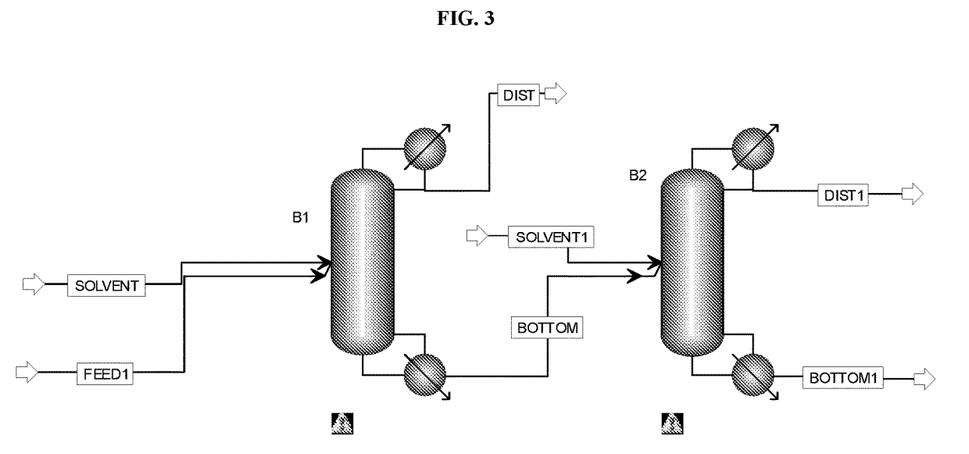
FIG. 3 depicts an exemplary state of the art system for producing 1,3-butadiene.

As shown in FIG. 3, the method for using two distillation columns to produce 1,3-butadiene includes feeding FEED1 to a first distillation column B1. In the first distillation column B1, the solvent, i.e., acetonitrile, was fed as stream SOLVENT. A stream including predominantly butane, butene-1, trans-2-butene and cis-2-butene was removed from the top of column B1 as stream DIST (Table 4). The bottom of B1 was fed to second distillation column B2. Acetonitrile was fed as stream SOLVENT1. In the second distillation column B2, a stream containing predominantly 1,2-butadiene and vinylacetylene was separated off at bottom product as stream BOTTOM1 (Table 4). A stream containing 1,3-butadiene was removed from the top of the second distillation column B2 as stream DIST1 (Table 4). Material balance and distillation column profiles of the two column distillation method is provided in Table 4 and the column profile of the two distillation column method is shown in Table 7.

As shown in Table 4, the method using two distinct distillation columns to produce 1,3-butadiene resulted in the production of a product stream that contained 85.2% 1,3-butadiene; whereas, the method of the disclosed subject matter resulted in a product stream that includes 93.4% 1,3-butadiene (Table 2).

TABLE 4

Material Balance of the Two Distillation Column Method

|  | FEED1 | SOLVENT | DIST | BOTTOM | SOLVENT1 | DIST1 | BOTTOM1 |
|---|---|---|---|---|---|---|---|
| Temperature (° C.) | 50 | 50 | 53.4 | 102.8 | 50 | 50.5 | 145.6 |
| Pressure (bar) | 1 | 2 | 7 | 7.5 | 2 | 6 | 6.4 |
| Vapor Fraction | 1 | 0 | 0 | 0 | 0 | 0 | 0 |
| Mole Flow (kmol/hr) | 18.111 | 150.763 | 9.75 | 159.124 | 150.763 | 8.8 | 301.087 |
| Mass Flow (kg/hr) | 1000 | 8000 | 546.411 | 8453.589 | 8000 | 476.305 | 15977.28 |
| Volume Flow (cm³/hr) | 477.979 | 10.015 | 0.967 | 11.82 | 10.015 | 0.804 | 23.926 |
| Enthalpy (MMBtu/hr) | 0.808 | 21.157 | −0.154 | 22.772 | 21.157 | 0.707 | 45.661 |
|  |  |  | MASS FLOW (KG/HR) |  |  |  |  |
| Acetonitrile |  | 8000 | 38.8 | 7961.2 | 8000 | 26.441 | 15934.76 |
| Water | 0.3 |  | trace | 0.3 |  | 0.3 | trace |

TABLE 4-continued

Material Balance of the Two Distillation Column Method

| | FEED1 | SOLVENT | DIST | BOTTOM | SOLVENT1 | DIST1 | BOTTOM1 |
|---|---|---|---|---|---|---|---|
| N-butane | 57.983 | | 57.982 | <0.001 | | <0.001 | trace |
| Iso-butene | 11.696 | | 11.696 | 0.001 | | 0.001 | trace |
| Butene-1 | 374.588 | | 374.583 | 0.004 | | 0.004 | trace |
| Trans-2-butene | 51.585 | | 48.696 | 2.888 | | 2.888 | trace |
| Cis-2-butene | 39.988 | | 2.958 | 37.03 | | 37.03 | trace |
| 1,3-butadiene | 452.864 | | 11.696 | 441.168 | | 405.642 | 35.526 |
| 1,2-butadiene | 3.999 | | trace | 3.999 | | 3.999 | <0.001 |
| Vinylacetylene | 6.998 | | trace | 6.998 | | trace | 6.998 |
| | | | MASS FRACTION | | | | |
| Acetonitrile | | 1 | 0.071 | 0.942 | 1 | 0.056 | 0.997 |
| Water | 300 PPM | | trace | 35 ppm | | 630 ppm | trace |
| N-butane | 0.058 | | 0.106 | 18 ppb | | 313 ppb | trace |
| Iso-butene | 0.012 | | 0.021 | 72 ppb | | 1 ppm | trace |
| Butene-1 | 0.375 | | 0.686 | 491 ppb | | 9 ppm | trace |
| Trans-2-butene | 0.052 | | 0.089 | 342 ppm | | 0.006 | trace |
| Cis-2-butene | 0.04 | | 0.005 | 0.004 | | 0.078 | trace |
| 1,3-butadiene | 0.453 | | 0.021 | 0.052 | | 0.852 | 0.002 |
| 1,2-butadiene | 0.004 | | 8 PPB | 473 ppm | | 0.008 | 6 ppb |
| Vinylacetylene | 0.007 | | trace | 828 ppm | | trace | 438 ppm |

Energy consumption for the method using two distinct distillation columns and the method using the divided wall distillation column are provided in Table 5. The divided wall distillation column process required 20% less heating energy and 40% less cooling energy compared to the two stage distillation column. In addition, as shown in Table 5, the capital expenditure of the divided wall distillation column is 30% lower and foot space is 40% lower than the method using two distillation columns. These data suggest that use of a method of the presently disclosed subject matter results in a reduction in capital and energy costs and results in a 1,3-butadiene product of higher purity.

TABLE 5

| | Two distillation columns | Divided wall distillation column |
|---|---|---|
| Number of shell | 2 | 1 |
| Number of equipment | 13 | 10 |
| Space required | — | 40% less |
| CAPEX | — | 30% less |
| Condenser energy required | 1.52 MW, 0.122 MW | 0.703 MW, 0.256 MW |
| Reboiler energy required | 1.714 MW, 0.837 MW | 2.01 MW |
| 1,3-butadiene in distillate | 85.16% w/w | 93.43% w/w |

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents. Various patents and patent applications are cited herein, the contents of which are hereby incorporated by reference herein in their entireties.

TABLE 6

Column Profile of the Divided Wall Distillation Column Method

| | Pre-fractionating column | | | | | Main Distillation Column | | | | |
|---|---|---|---|---|---|---|---|---|---|---|
| Stage | Temperature C. | Pressure bar | Heat duty Gcal/hr | Liquid from (Mole) kmol/hr | Vapor from (Mole) kmol/hr | Stage | Temperature C. | Pressure bar | Heat duty Gcal/hr | Liquid from (Mole) kmol/hr | Vapor from (Mole) kmol/hr |
| 1 | 54.05449 | 7 | −0.60508 | 129.9472 | 0 | 1 | 55.82591 | 7 | −0.22055 | 47.45051 | 0 |
| 2 | 54.3857 | 7.006757 | 0 | 118.719 | 129.9472 | 2 | 55.94444 | 7.007246 | 0 | 36.33168 | 47.45051 |
| 3 | 54.82577 | 7.013514 | 0 | 275.9121 | 129.5479 | 3 | 68.10144 | 7.014493 | 0 | 229.0071 | 43.57604 |
| 4 | 55.14338 | 7.02027 | 0 | 275.9702 | 135.9785 | 4 | 68.12856 | 7.021739 | 0 | 229.048 | 66.64355 |
| 5 | 55.4624 | 7.027027 | 0 | 276.0535 | 136.0365 | 5 | 68.15841 | 7.028986 | 0 | 229.0934 | 66.68447 |
| 6 | 55.77912 | 7.033784 | 0 | 276.1654 | 136.1198 | 6 | 68.18927 | 7.036232 | 0 | 229.1371 | 66.72984 |
| 7 | 56.08973 | 7.040541 | 0 | 276.3084 | 136.2318 | 7 | 68.22087 | 7.043478 | 0 | 229.179 | 66.77357 |
| 8 | 56.39046 | 7.047297 | 0 | 276.4831 | 136.3747 | 8 | 68.25387 | 7.050725 | 0 | 229.2251 | 66.81539 |
| 9 | 56.6776 | 7.054054 | 0 | 276.6882 | 136.5494 | 9 | 68.28742 | 7.057971 | 0 | 229.2725 | 66.86151 |
| 10 | 56.94753 | 7.060811 | 0 | 276.9198 | 136.7545 | 10 | 68.32081 | 7.065217 | 0 | 229.3172 | 66.90898 |

TABLE 6-continued

Column Profile of the Divided Wall Distillation Column Method

| | Pre-fractionating column | | | | | Main Distillation Column | | | | |
|---|---|---|---|---|---|---|---|---|---|---|
| Stage | Temperature C. | Pressure bar | Heat duty Gcal/hr | Liquid from (Mole) kmol/hr | Vapor from (Mole) kmol/hr | Stage | Temperature C. | Pressure bar | Heat duty Gcal/hr | Liquid from (Mole) kmol/hr | Vapor from (Mole) kmol/hr |
| 11 | 57.19688 | 7.067568 | 0 | 277.1715 | 136.9861 | 11 | 68.35447 | 7.072464 | 0 | 229.3615 | 66.95368 |
| 12 | 57.42281 | 7.074324 | 0 | 277.4349 | 137.2379 | 12 | 68.38846 | 7.07971 | 0 | 229.4043 | 66.99791 |
| 13 | 57.62341 | 7.081081 | 0 | 277.7004 | 137.5013 | 13 | 68.42757 | 7.086957 | 0 | 229.453 | 67.04071 |
| 14 | 57.79805 | 7.087838 | 0 | 277.9589 | 137.7668 | 14 | 68.46375 | 7.094203 | 0 | 229.502 | 67.08942 |
| 15 | 57.94748 | 7.094595 | 0 | 278.2029 | 138.0253 | 15 | 68.50018 | 7.101449 | 0 | 229.5515 | 67.13845 |
| 16 | 58.07368 | 7.101351 | 0 | 278.4271 | 138.2692 | 16 | 68.53579 | 7.108696 | 0 | 229.6001 | 67.18792 |
| 17 | 58.17948 | 7.108108 | 0 | 278.6288 | 138.4934 | 17 | 68.56981 | 7.115942 | 0 | 229.645 | 67.23652 |
| 18 | 58.26815 | 7.114865 | 0 | 278.8076 | 138.6951 | 18 | 68.60269 | 7.123188 | 0 | 229.6864 | 67.28147 |
| 19 | 58.343 | 7.121622 | 0 | 278.9647 | 138.874 | 19 | 68.63553 | 7.130435 | 0 | 229.7311 | 67.3228 |
| 20 | 58.40709 | 7.128378 | 0 | 279.1022 | 139.031 | 20 | 68.66467 | 7.137681 | 0 | 229.7616 | 67.3675 |
| 21 | 58.46307 | 7.135135 | 0 | 279.2228 | 139.1685 | 21 | 68.69758 | 7.144928 | 0 | 229.8056 | 67.39801 |
| 22 | 58.51312 | 7.141892 | 0 | 279.3293 | 139.2891 | 22 | 68.72193 | 7.152174 | 0 | 229.8412 | 67.44206 |
| 23 | 58.559 | 7.148649 | 0 | 279.4243 | 139.3956 | 23 | 68.75606 | 7.15942 | 0 | 229.8778 | 67.4776 |
| 24 | 58.60201 | 7.155405 | 0 | 279.5104 | 139.4907 | 24 | 68.79035 | 7.166667 | 0 | 229.9225 | 67.51424 |
| 25 | 58.64315 | 7.162162 | 0 | 279.5894 | 139.5767 | 25 | 68.82315 | 7.173913 | 0 | 229.9635 | 67.55896 |
| 26 | 58.68311 | 7.168919 | 0 | 279.6631 | 139.6558 | 26 | 68.85569 | 7.181159 | 0 | 230.0075 | 67.59997 |
| 27 | 58.72238 | 7.175676 | 0 | 279.7327 | 139.7295 | 27 | 68.88752 | 7.188406 | 0 | 230.0427 | 67.64391 |
| 28 | 58.76129 | 7.182432 | 0 | 279.7991 | 139.799 | 28 | 68.91829 | 7.195652 | 0 | 230.0725 | 67.67914 |
| 29 | 58.80005 | 7.189189 | 0 | 279.863 | 139.8654 | 29 | 68.9489 | 7.202899 | 0 | 230.1051 | 67.70894 |
| 30 | 58.83879 | 7.195946 | 0 | 279.9249 | 139.9294 | 30 | 68.97863 | 7.210145 | 0 | 230.1343 | 67.74152 |
| 31 | 58.87755 | 7.202703 | 0 | 279.985 | 139.9913 | 31 | 69.00762 | 7.217391 | 0 | 230.1637 | 67.77074 |
| 32 | 58.91639 | 7.209459 | 0 | 280.0436 | 140.0514 | 32 | 69.03744 | 7.224638 | 0 | 230.1587 | 67.80017 |
| 33 | 58.9553 | 7.216216 | 0 | 280.1005 | 140.1099 | 33 | 69.07132 | 7.231884 | 0 | 230.197 | 67.7951 |
| 34 | 58.99431 | 7.222973 | 0 | 280.1559 | 140.1669 | 34 | 69.10634 | 7.23913 | 0 | 230.2799 | 67.83341 |
| 35 | 59.03349 | 7.22973 | 0 | 280.2096 | 140.2222 | 35 | 69.13958 | 7.246377 | 0 | 230.3227 | 67.9163 |
| 36 | 59.07304 | 7.236486 | 0 | 280.2613 | 140.2759 | 36 | 69.17277 | 7.253623 | 0 | 230.3654 | 67.95913 |
| 37 | 59.11328 | 7.243243 | 0 | 280.3142 | 140.3277 | 37 | 69.20584 | 7.26087 | 0 | 230.4067 | 68.00183 |
| 38 | 59.15122 | 7.25 | 0 | 280.4361 | 140.3805 | 38 | 69.2405 | 7.268116 | 0 | 230.4625 | 68.04312 |
| 39 | 59.1138 | 7.256757 | 0 | 280.9031 | 140.5024 | 39 | 69.26848 | 7.275362 | 0 | 230.4723 | 68.09897 |
| 40 | 59.49861 | 7.263514 | 0 | 281.3 | 122.8691 | 40 | 69.30391 | 7.282609 | 0 | 230.5311 | 68.10873 |
| 41 | 59.80658 | 7.27027 | 0 | 281.6356 | 123.2661 | 41 | 69.33627 | 7.289855 | 0 | 230.5691 | 68.16757 |
| 42 | 60.04612 | 7.277027 | 0 | 281.9101 | 123.6017 | 42 | 69.36988 | 7.297101 | 0 | 230.6096 | 68.2055 |
| 43 | 60.2298 | 7.283784 | 0 | 282.1309 | 123.8762 | 43 | 69.40708 | 7.304348 | 0 | 230.6703 | 68.24602 |
| 44 | 60.37052 | 7.290541 | 0 | 282.308 | 124.097 | 44 | 69.44156 | 7.311594 | 0 | 230.7201 | 68.3067 |
| 45 | 60.4795 | 7.297297 | 0 | 282.4512 | 124.2741 | 45 | 69.47495 | 7.318841 | 0 | 230.7653 | 68.35657 |
| 46 | 60.56568 | 7.304054 | 0 | 282.5689 | 124.4173 | 46 | 69.50829 | 7.326087 | 0 | 230.8117 | 68.40172 |
| 47 | 60.63581 | 7.310811 | 0 | 282.6674 | 124.535 | 47 | 69.54047 | 7.333333 | 0 | 230.8536 | 68.44817 |
| 48 | 60.69478 | 7.317568 | 0 | 282.7517 | 124.6335 | 48 | 69.56759 | 7.34058 | 0 | 230.8821 | 68.49004 |
| 49 | 60.74607 | 7.324324 | 0 | 282.8253 | 124.7178 | 49 | 69.60666 | 7.347826 | 0 | 230.9404 | 68.51857 |
| 50 | 60.79212 | 7.331081 | 0 | 282.891 | 124.7914 | 50 | 69.63401 | 7.355072 | 0 | 230.9691 | 68.5768 |
| 51 | 60.83467 | 7.337838 | 0 | 282.9505 | 124.857 | 51 | 69.67129 | 7.362319 | 0 | 231.0179 | 68.60554 |
| 52 | 60.8749 | 7.344595 | 0 | 283.0056 | 124.9166 | 52 | 69.70395 | 7.369565 | 0 | 231.0609 | 68.65434 |
| 53 | 60.91366 | 7.351351 | 0 | 283.0573 | 124.9716 | 53 | 69.73559 | 7.376812 | 0 | 231.0981 | 68.69734 |
| 54 | 60.95156 | 7.358108 | 0 | 283.1067 | 125.0233 | 54 | 69.76719 | 7.384058 | 0 | 231.1345 | 68.7345 |
| 55 | 60.98904 | 7.364865 | 0 | 283.1546 | 125.0727 | 55 | 69.79937 | 7.391304 | 0 | 231.174 | 68.77093 |
| 56 | 61.02643 | 7.371622 | 0 | 283.2017 | 125.1206 | 56 | 69.83193 | 7.398551 | 0 | 231.2159 | 68.81046 |
| 57 | 61.06398 | 7.378378 | 0 | 283.2488 | 125.1678 | 57 | 69.86455 | 7.405797 | 0 | 231.2582 | 68.85232 |
| 58 | 61.10188 | 7.385135 | 0 | 283.2962 | 125.2148 | 58 | 69.89737 | 7.413043 | 0 | 231.3028 | 68.89467 |
| 59 | 61.14029 | 7.391892 | 0 | 283.3444 | 125.2623 | 59 | 69.9289 | 7.42029 | 0 | 231.3423 | 68.93924 |
| 60 | 61.17934 | 7.398649 | 0 | 283.3936 | 125.3104 | 60 | 69.95367 | 7.427536 | 0 | 231.3612 | 68.97872 |
| 61 | 61.21912 | 7.405405 | 0 | 283.444 | 125.3597 | 61 | 70.00372 | 7.434783 | 0 | 231.4256 | 68.99767 |
| 62 | 61.25972 | 7.412162 | 0 | 283.4956 | 125.4101 | 62 | 70.06389 | 7.442029 | 0 | 231.4335 | 69.062 |
| 63 | 61.30121 | 7.418919 | 0 | 283.5482 | 125.4616 | 63 | 70.24022 | 7.449275 | 0 | 231.2581 | 69.06993 |
| 64 | 61.34362 | 7.425676 | 0 | 283.6016 | 125.5143 | 64 | 71.07596 | 7.456522 | 0 | 230.1304 | 68.89453 |
| 65 | 61.387 | 7.432432 | 0 | 283.6555 | 125.5677 | 65 | 75.50065 | 7.463768 | 0 | 226.4678 | 67.76681 |
| 66 | 61.43139 | 7.439189 | 0 | 283.7093 | 125.6216 | 66 | 93.92581 | 7.471014 | 0 | 228.671 | 64.10427 |
| 67 | 61.47683 | 7.445946 | 0 | 283.7626 | 125.6754 | 67 | 127.8533 | 7.478261 | 0 | 252.9244 | 66.30747 |
| 68 | 61.52338 | 7.452703 | 0 | 283.8147 | 125.7286 | 68 | 146.6308 | 7.485507 | 0 | 272.4978 | 90.56086 |
| 69 | 61.57118 | 7.459459 | 0 | 283.8649 | 125.7807 | 69 | 151.0731 | 7.492754 | 0 | 277.7061 | 110.1342 |
| 70 | 61.62058 | 7.466216 | 0 | 283.9115 | 125.831 | 70 | 151.9513 | 7.5 | 1.731389 | 320.3959 | 220.6974 |
| 71 | 61.67347 | 7.472973 | 0 | 283.9369 | 125.8776 | | | | | | |
| 72 | 61.75147 | 7.47973 | 0 | 283.6857 | 125.903 | | | | | | |
| 73 | 62.17228 | 7.486486 | 0 | 279.537 | 125.6518 | | | | | | |
| 74 | 67.66271 | 7.493243 | 0 | 254.7611 | 121.503 | | | | | | |
| 75 | 108.2874 | 7.5 | 0 | 263.3872 | 96.72717 | | | | | | |

TABLE 7

Column Profile of the Two Distillation Column Method

| | Column B1 | | | | | | Column B2 | | | | |
|---|---|---|---|---|---|---|---|---|---|---|---|
| Stage | Temperature C. | Pressure bar | Heat duty Gcal/hr | Liquid from (Mole) kmol/hr | Vapor from (Mole) kmol/hr | Stage | Temperature C. | Pressure bar | Heat duty Gcal/hr | Liquid from (Mole) kmol/hr | Vapor From (Mole) kmol/hr |
| 1 | 53.43672 | 7 | −1.30961 | 282.7571 | 0 | 1 | 50.5247 | 6 | −0.10511 | 21.99895 | 0 |
| 2 | 53.68163 | 7.006757 | 0 | 429.2006 | 282.7571 | 2 | 50.90189 | 6.00678 | 0 | 10.50991 | 21.99895 |
| 3 | 53.90336 | 7.013514 | 0 | 429.0807 | 288.1883 | 3 | 70.57122 | 6.013559 | 0 | 181.8565 | 19.30949 |
| 4 | 54.12939 | 7.02027 | 0 | 428.9293 | 288.0684 | 4 | 71.00091 | 6.020339 | 0 | 182.3288 | 39.8935 |
| 5 | 54.36189 | 7.027027 | 0 | 428.7772 | 287.917 | 5 | 71.1705 | 6.027119 | 0 | 182.5089 | 40.36576 |
| 6 | 54.60015 | 7.033784 | 0 | 428.6305 | 287.7649 | 6 | 71.25104 | 6.033898 | 0 | 182.5909 | 40.54587 |
| 7 | 54.84114 | 7.040541 | 0 | 428.4823 | 287.6182 | 7 | 71.30078 | 6.040678 | 0 | 182.629 | 40.62785 |
| 8 | 55.08339 | 7.047297 | 0 | 428.3353 | 287.4699 | 8 | 71.33492 | 6.047458 | 0 | 182.6686 | 40.666 |
| 9 | 55.32734 | 7.054054 | 0 | 428.2143 | 287.323 | 9 | 71.36463 | 6.054237 | 0 | 182.7068 | 40.70559 |
| 10 | 55.56896 | 7.060811 | 0 | 428.1002 | 287.2019 | 10 | 71.3926 | 6.061017 | 0 | 182.7329 | 40.74374 |
| 11 | 55.80611 | 7.067568 | 0 | 427.9979 | 287.0879 | 11 | 71.42321 | 6.067797 | 0 | 182.7722 | 40.76985 |
| 12 | 56.03733 | 7.074324 | 0 | 427.9114 | 286.9855 | 12 | 71.45411 | 6.074576 | 0 | 182.8193 | 40.80917 |
| 13 | 56.26107 | 7.081081 | 0 | 427.8423 | 286.8991 | 13 | 71.47205 | 6.081356 | 0 | 182.8388 | 40.85628 |
| 14 | 56.47613 | 7.087838 | 0 | 427.793 | 286.8299 | 14 | 71.49894 | 6.088136 | 0 | 182.8708 | 40.8758 |
| 15 | 56.6808 | 7.094595 | 0 | 427.7614 | 286.7807 | 15 | 71.52686 | 6.094915 | 0 | 182.8981 | 40.90779 |
| 16 | 56.87334 | 7.101351 | 0 | 427.7326 | 286.7491 | 16 | 71.57024 | 6.101695 | 0 | 182.9527 | 40.93504 |
| 17 | 57.05812 | 7.108108 | 0 | 427.7461 | 286.7203 | 17 | 71.59473 | 6.108475 | 0 | 182.9627 | 40.98966 |
| 18 | 57.2312 | 7.114865 | 0 | 427.7755 | 286.7337 | 18 | 71.62135 | 6.115254 | 0 | 182.9835 | 40.99966 |
| 19 | 57.39098 | 7.121622 | 0 | 427.8236 | 286.7631 | 19 | 71.6493 | 6.122034 | 0 | 183.0121 | 41.02047 |
| 20 | 57.53586 | 7.128378 | 0 | 427.8868 | 286.8112 | 20 | 71.6778 | 6.128814 | 0 | 183.0453 | 41.04911 |
| 21 | 57.66802 | 7.135135 | 0 | 427.944 | 286.8745 | 21 | 71.70595 | 6.135593 | 0 | 183.0766 | 41.08231 |
| 22 | 57.79061 | 7.141892 | 0 | 428.0586 | 286.9317 | 22 | 71.73394 | 6.142373 | 0 | 183.1047 | 41.11361 |
| 23 | 57.89267 | 7.148649 | 0 | 428.1313 | 287.0462 | 23 | 71.76196 | 6.149153 | 0 | 183.1321 | 41.14172 |
| 24 | 57.99127 | 7.155405 | 0 | 428.2337 | 287.1189 | 24 | 71.79004 | 6.155932 | 0 | 183.1613 | 41.16913 |
| 25 | 58.08311 | 7.162162 | 0 | 428.3336 | 287.2213 | 25 | 71.81872 | 6.162712 | 0 | 183.193 | 41.19825 |
| 26 | 58.16899 | 7.168919 | 0 | 428.4659 | 287.3213 | 26 | 71.84602 | 6.169492 | 0 | 183.2275 | 41.22998 |
| 27 | 58.26469 | 7.175676 | 0 | 428.6692 | 287.4535 | 27 | 71.87002 | 6.176271 | 0 | 183.2495 | 41.26444 |
| 28 | 58.31798 | 7.182432 | 0 | 428.7423 | 287.6568 | 28 | 71.89699 | 6.183051 | 0 | 183.2795 | 41.28653 |
| 29 | 58.36918 | 7.189189 | 0 | 428.9105 | 287.73 | 29 | 71.92826 | 6.189831 | 0 | 183.3091 | 41.31649 |
| 30 | 58.41593 | 7.195946 | 0 | 429.0138 | 287.8982 | 30 | 71.95274 | 6.19661 | 0 | 183.3384 | 41.34605 |
| 31 | 58.46327 | 7.202703 | 0 | 429.2114 | 288.0015 | 31 | 71.9833 | 6.20339 | 0 | 183.3677 | 41.37535 |
| 32 | 58.50697 | 7.209459 | 0 | 429.3391 | 288.1991 | 32 | 72.01597 | 6.210169 | 0 | 183.4046 | 41.4047 |
| 33 | 58.53157 | 7.216216 | 0 | 429.4908 | 288.3268 | 33 | 72.04299 | 6.216949 | 0 | 183.4315 | 41.44156 |
| 34 | 58.56103 | 7.222973 | 0 | 429.6257 | 288.4785 | 34 | 72.07134 | 6.223729 | 0 | 183.4572 | 41.46851 |
| 35 | 58.58724 | 7.22973 | 0 | 429.7646 | 288.6133 | 35 | 72.0992 | 6.230508 | 0 | 183.4866 | 41.49415 |
| 36 | 58.61111 | 7.236486 | 0 | 429.9217 | 288.7523 | 36 | 72.12742 | 6.237288 | 0 | 183.5162 | 41.52356 |
| 37 | 58.63037 | 7.243243 | 0 | 430.0541 | 288.9094 | 37 | 72.1559 | 6.244068 | 0 | 183.5466 | 41.55318 |
| 38 | 58.64994 | 7.25 | 0 | 430.1592 | 289.0418 | 38 | 72.18437 | 6.250847 | 0 | 183.5798 | 41.58362 |
| 39 | 58.66542 | 7.256757 | 0 | 430.7025 | 289.1469 | 39 | 72.21211 | 6.257627 | 0 | 183.6172 | 41.61675 |
| 40 | 58.84851 | 7.263514 | 0 | 430.795 | 271.5787 | 40 | 72.23538 | 6.264407 | 0 | 183.6379 | 41.65415 |
| 41 | 59.00687 | 7.27027 | 0 | 430.8721 | 271.6711 | 41 | 72.26285 | 6.271186 | 0 | 183.6678 | 41.67492 |
| 42 | 59.14443 | 7.277027 | 0 | 430.94 | 271.7483 | 42 | 72.29067 | 6.277966 | 0 | 183.6977 | 41.70481 |
| 43 | 59.26895 | 7.283784 | 0 | 431.0241 | 271.8161 | 43 | 72.31873 | 6.284746 | 0 | 183.7272 | 41.73473 |
| 44 | 59.3788 | 7.290541 | 0 | 431.1084 | 271.9002 | 44 | 72.35025 | 6.291525 | 0 | 183.755 | 41.76421 |
| 45 | 59.4759 | 7.297297 | 0 | 431.1926 | 271.9846 | 45 | 72.39683 | 6.298305 | 0 | 183.8038 | 41.79198 |
| 46 | 59.56074 | 7.304054 | 0 | 431.2972 | 272.0687 | 46 | 72.46652 | 6.305085 | 0 | 183.8122 | 41.84083 |
| 47 | 59.63682 | 7.310811 | 0 | 431.3668 | 272.1734 | 47 | 72.67876 | 6.311864 | 0 | 183.7799 | 41.84919 |
| 48 | 59.70714 | 7.317568 | 0 | 431.4579 | 272.243 | 48 | 73.49997 | 6.318644 | 0 | 183.6046 | 41.81689 |
| 49 | 59.76792 | 7.324324 | 0 | 431.5368 | 272.334 | 49 | 76.78254 | 6.325424 | 0 | 183.2943 | 41.64162 |
| 50 | 59.82438 | 7.331081 | 0 | 431.6161 | 272.4129 | 50 | 87.21742 | 6.332203 | 0 | 338.9774 | 39.10865 |
| 51 | 59.87741 | 7.337838 | 0 | 431.7057 | 272.4922 | 51 | 87.40334 | 6.338983 | 0 | 339.3537 | 37.89057 |
| 52 | 59.92652 | 7.344595 | 0 | 431.7792 | 272.5819 | 52 | 87.48197 | 6.345763 | 0 | 339.5121 | 38.26683 |
| 53 | 59.97161 | 7.351351 | 0 | 431.8668 | 272.6554 | 53 | 87.53156 | 6.352542 | 0 | 339.5996 | 38.42521 |
| 54 | 60.01229 | 7.358108 | 0 | 431.9254 | 272.743 | 54 | 87.60682 | 6.359322 | 0 | 339.6772 | 38.51273 |
| 55 | 60.05076 | 7.364865 | 0 | 432.0125 | 272.8015 | 55 | 87.86107 | 6.366102 | 0 | 339.824 | 38.59038 |
| 56 | 60.0896 | 7.371622 | 0 | 432.0786 | 272.8887 | 56 | 88.97072 | 6.372881 | 0 | 340.3797 | 38.73712 |
| 57 | 60.13047 | 7.378378 | 0 | 432.1848 | 272.9548 | 57 | 93.75623 | 6.379661 | 0 | 343.4446 | 39.29288 |
| 58 | 60.16426 | 7.385135 | 0 | 432.2186 | 273.061 | 58 | 109.5168 | 6.386441 | 0 | 358.6754 | 42.35772 |
| 59 | 60.2016 | 7.391892 | 0 | 432.3295 | 273.0948 | 59 | 133.7282 | 6.39322 | 0 | 391.4129 | 57.58852 |
| 60 | 60.24269 | 7.398649 | 0 | 432.4016 | 273.2056 | 60 | 145.5709 | 6.4 | 0.719654 | 301.0869 | 90.32606 |
| 61 | 60.27496 | 7.405405 | 0 | 432.4642 | 273.2778 | | | | | | |
| 62 | 60.31057 | 7.412162 | 0 | 432.55 | 273.3404 | | | | | | |
| 63 | 60.34457 | 7.418919 | 0 | 432.6066 | 273.4262 | | | | | | |
| 64 | 60.38061 | 7.425676 | 0 | 432.6974 | 273.4828 | | | | | | |
| 65 | 60.41466 | 7.432432 | 0 | 432.7371 | 273.5736 | | | | | | |
| 66 | 60.45576 | 7.439189 | 0 | 432.814 | 273.6132 | | | | | | |
| 67 | 60.49815 | 7.445946 | 0 | 432.8831 | 273.6902 | | | | | | |
| 68 | 60.54182 | 7.452703 | 0 | 432.9516 | 273.7593 | | | | | | |
| 69 | 60.58211 | 7.459459 | 0 | 433.0306 | 273.8277 | | | | | | |
| 70 | 60.62135 | 7.466216 | 0 | 432.9949 | 273.9068 | | | | | | |
| 71 | 60.68224 | 7.472973 | 0 | 433.0149 | 273.8711 | | | | | | |
| 72 | 60.75556 | 7.47973 | 0 | 432.7863 | 273.8911 | | | | | | |

TABLE 7-continued

Column Profile of the Two Distillation Column Method

| | Column B1 | | | | | | Column B2 | | | | |
|---|---|---|---|---|---|---|---|---|---|---|---|
| Stage | Temperature C. | Pressure bar | Heat duty Gcal/hr | Liquid from (Mole) kmol/hr | Vapor from (Mole) kmol/hr | Stage | Temperature C. | Pressure bar | Heat duty Gcal/hr | Liquid from (Mole) kmol/hr | Vapor From (Mole) kmol/hr |
| 73 | 60.9275 | 7.486486 | 0 | 428.6334 | 273.6624 | | | | | | |
| 74 | 62.92806 | 7.493243 | 0 | 365.9849 | 269.5095 | | | | | | |
| 75 | 102.7604 | 7.5 | 1.474464 | 159.1238 | 206.861 | | | | | | |

The invention claimed is:

1. A method for extractive distillation of 1,3-butadiene, the method comprising the steps of:
   (a) providing a distillation column that comprises a longitudinal wall dividing the distillation column into a first region, a second region and a combined bottom region, a first condenser coupled to the first region, a second condenser coupled to the second region and a reboiler coupled to the combined bottom region;
   (b) feeding a $C_4$ hydrocarbon stream comprising at least one compound selected from the group consisting of $C_4$ alkanes, $C_4$ alkenes, $C_4$ alkadienes, $C_4$ alkynes and combinations thereof into the first region of the distillation column, wherein:
      i. the $C_4$ hydrocarbon stream is split into two or more streams, and the two or more streams are fed into the first region at multiple locations; or
      ii. the $C_4$ hydrocarbon stream comprises at least one compound selected from the group consisting of 1,3-butadiene, butane, isobutane, 1-butene, trans-2-butene, cis-2-butene, isobutene, 1,2-butadiene, vinylacetylene, ethylacetylene, and combinations thereof;
   (c) feeding a first solvent into the first region of the distillation column;
   (d) removing a first stream from the first region of the distillation column;
   (e) feeding a second solvent into the second region of the distillation column;
   (f) removing a second stream from the second region of the distillation column, wherein the second stream contains 1,3-butadiene and wherein the second stream is removed from a top of the second region; and
   (g) removing a third stream from the combined bottom region of the distillation column; and
   (h) adding a polymerization inhibitor to at least one of the first region, the second region, and the combined bottom region of the distillation column.

2. The method of claim 1, wherein the third stream further comprises 1,3-butadiene.

3. The method of claim 2, further comprising:
   (a) separating 1,3-butadiene, the first solvent and/or the second solvent from the third stream; and
   (b) recycling 1,3-butadiene, the first solvent and/or the second solvent back to the combined bottom region of the distillation column.

4. The method of claim 3, wherein the first solvent and/or the second solvent are separated by vaporization.

5. The method of claim 1, wherein the $C_4$ hydrocarbon stream is fed into a middle section of the first region of the distillation column.

6. The method of claim 1, wherein the first solvent is fed into an upper section of the first region of the distillation column or wherein the second solvent is fed into an upper section of the second region of the distillation column.

7. The method of claim 1, wherein the first stream is removed from the first region of the distillation column using the first condenser or wherein the second stream is removed from the second region of the distillation column using the second condenser.

8. The method of claim 7, further comprising transferring a first reflux fluid from the first condenser to the first region of the distillation column or further comprising transferring a second reflux fluid from the second condenser to the second region of the distillation column.

9. The method of claim 1, wherein the first and/or second solvent comprises acetonitrile.

10. The method of claim 1, wherein the second stream comprises 1,2-butadiene.

11. The method of claim 1, wherein the first region of the distillation column has at least about 75 equilibrium stages or wherein the second region of the distillation column has at least about 70 equilibrium stages.

12. The method of claim 1, wherein an upper section of the first region and/or second region of the distillation column has a pressure of about −1.0 to about 15.0 bar.

13. The method of claim 12, wherein the combined bottom region of the distillation column has a pressure of about 15.0 bar and optionally wherein the pressure of the combined bottom region is greater than the pressure of the upper section of the first region and/or second region by about 0.01 to about 2 bar.

14. The method of claim 1, further comprising adding a polymerization inhibitor to the first region.

15. The method of claim 1, wherein the first solvent is introduced at a point above the C4 hydrocarbon stream.

16. A method for extractive distillation of 1,3-butadiene, the method comprising the steps of:
   (a) providing a distillation column that comprises a longitudinal wall dividing the distillation column into a first region, a second region and a combined bottom region, a first condenser coupled to the first region, a second condenser coupled to the second region and a reboiler coupled to the combined bottom region;
   (b) feeding a $C_4$ hydrocarbon stream comprising at least one compound selected from the group consisting of $C_4$ alkanes, $C_4$ alkenes, $C_4$ alkadienes, $C_4$ alkynes and combinations thereof into the first region of the distillation column, wherein:
      i. the $C_4$ hydrocarbon stream is split into two or more streams, and the two or more streams are fed into the first region at multiple locations; or
      ii. the $C_4$ hydrocarbon stream comprises one or more compounds selected from the group consisting of 1,3-butadiene, butane, isobutane, 1-butene, trans-2- butene, cis-2-butene, isobutene, 1,2-butadiene, vinylacetylene, ethylacetylene, and combinations thereof;

(c) feeding a first solvent into the first region of the distillation column;

(d) removing a first stream from the first region of the distillation column;

(e) feeding a second solvent into the second region of the distillation column;

(f) removing a second stream from the second region of the distillation column, wherein the second stream contains 1,3-butadiene and wherein the second stream is removed from a top of the second region; and (g) removing a third stream from the combined bottom region of the distillation column, wherein an upper section of the first region and/or second region of the distillation column has a pressure of about −1.0 bar.

* * * * *